July 31, 1973 G. DE RUITER Plant Pat. 3,383
ROSE PLANT
Filed Feb. 23, 1972
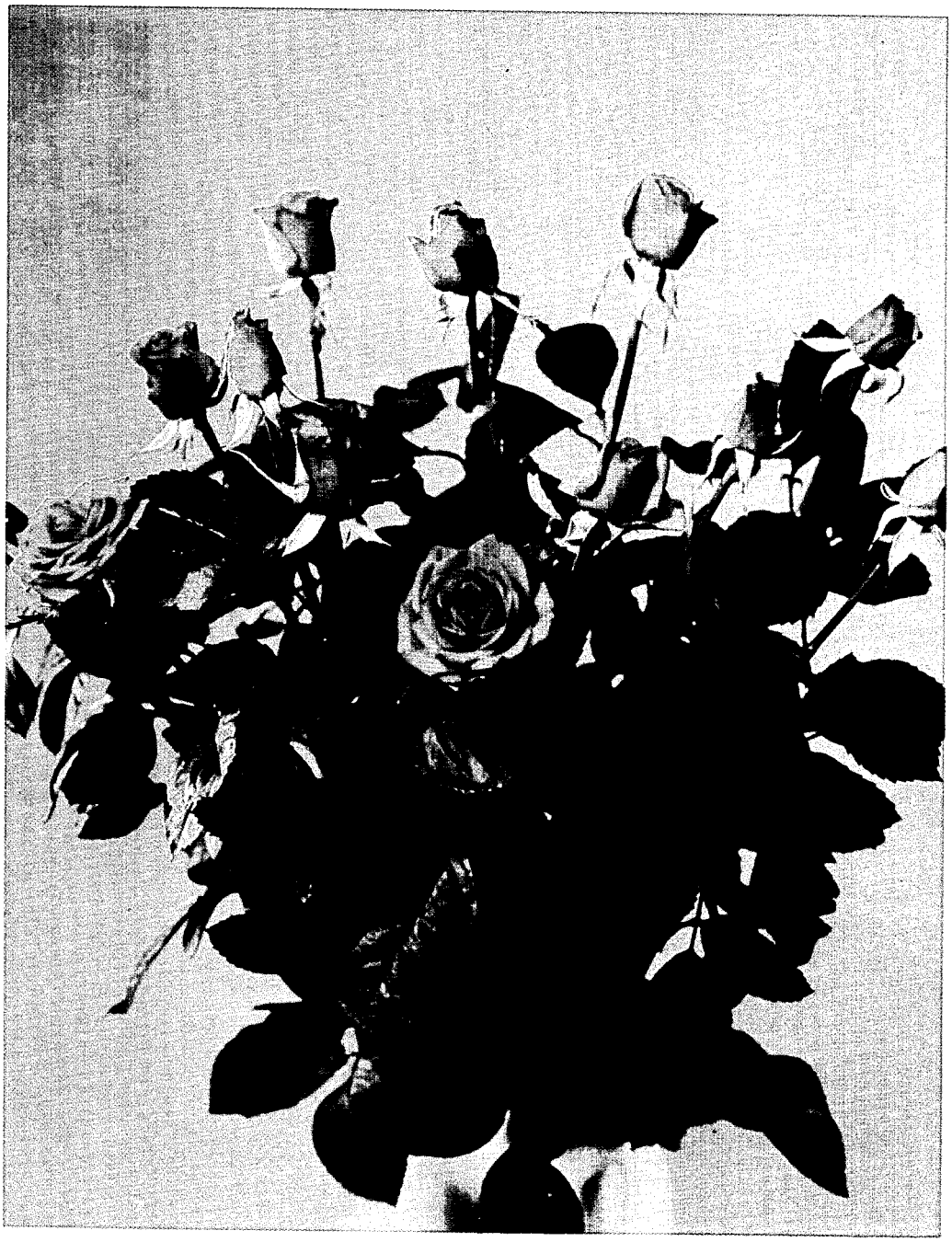

United States Patent Office

Plant Pat. 3,383
Patented July 31, 1973

3,383
ROSE PLANT

Gijsbert de Ruiter, Hazerswoude, Netherlands, assignor to Carlton Rose Nurseries, Carlton, Oreg.

Filed Feb. 23, 1972, Ser. No. 228,779
Int. Cl. A01h 5/00
U.S. Cl. Plt.—29 1 Claim

ABSTRACT OF THE DISCLOSURE

A rose plant of the floribunda class for greenhouse use as cut flowers, originated by crossing, as a seed parent, an unnamed seedling which was a cross between Mandrina, as a seed parent with Baccara (Plant Patent No. 1,367), as a pollen parent, which first-named seedling was crossed on an unnamed seedling as a pollen parent, which latter was also a cross between Mandrina, as a seed parent on Baccara (Plant Patent No. 1,367), as a pollen parent.

BACKGROUND OF DISCLOSURE

The present invention relates to a new and distinct variety of rose plant of the floribunda class, particularly for greenhouse growing of cut flowers, which was originated by me by crossing a seed parent, which was an unnamed seedling produced by Mandrina crossed on Baccarra (Plant Patent No. 1,367), on a pollen parent, which was a second unnamed seedling produced by crossing Mandrina on Baccara (Plant Patent No. 1,367).

The primary objective of this breeding was to produce a new rose variety which would grow tall in the greenhouse for cut flowers and would provide the distinctive and desirable characteristics suitable for this purpose.

Asexual reproduction of my new variety at Portland, Oreg., shows that the characteristics come true to form and that the distinguishing characteristics hold through succeeding propagations by budding.

BRIEF DESCRIPTION OF DRAWINGS

The accompanying drawing shows typical specimens of the growth and flower of my new variety in different stages of development and as depicted in color as nearly true as it is possible to make the same in color illustrations of this character.

DETAILED DESCRIPTION OF DISCLOSURE

The following is a detailed description of my new variety, with color terminology in accordance with the Dictionary of Color by A. Maerz and M. Rea Paul.

Type: Hardy; tall bush, greenhouse; seedling; for cut flowers.
Class: Floribunda.
Propagation: It does hold its distinguishing characteristics through succeeding propagations by cuttings, grafting and budding.

*Flower*

Locality where grown: Portland, Oreg.
Flowers Borne: Singly, several to stems; medium long stems.
Quantity of bloom: Abundant, in greenhouse.
Continuity: Continuous.
Fragrance: Slight, spicy.
Bud: Peduncle: Medium length; medium heavy; erect; stiff; green; smooth.
*Before calyx breaks.*—Size: medium. Form: short; globular; with few foliaceous appendages; with few slender medium parts extending beyond the tip of the bud.
*As calyx breaks.*—Color: Garnet or Wild Strawberry, Plate 6, K–6.

*As first petal opens.*—Size: medium, Form: flat pointed. Color: Outside: Garnet or Wild Strawberry, Plate 6, K–6. Inside: Afghan Red or Checkerberry, Plate 5, L–6.
*Opening.*—It does open up well.
Bloom: Size when fully open: medium large, 2½ inches to 3½ inches.
*Petalage.* Double, very double (many petals, usually with no stamens showing); from 30 to 35 petals; arranged regularly.
*Form.* Globular at first; becoming flat; petals remaining at first tightly cupped; becoming later at maturity tightly flat, rolled outward.
Petals: Thick; with inside velvety; outside velvety.
Shape: Outer: round. Intermediate: round. Inner: round with 1 notch.

This description of a newly opened flower was made from a rose grown in a greenhouse in August 1971, at Portland, Oreg.

Color:
*Outer petal.*—Outside surface: Garnet or Wild Strawberry, Plate 6, K–6. Inside surface: Afghan Red or Checkerberry, Plate 5, L–6.
*Intermediate petal.*—Outside surface: Sultan, Plate 4, K–6. Inside surface: Flaming Maple, Plate 4, L–5.
*Inner petal.*—Outside surface: Garnet Red of Wild Strawberry, Plate 6, K–6. Inside surface: Red Cross, Plate 4, L–6.

This description was made from a rose that was open for three days in a greenhouse in August 1971, at Portland, Oreg.

Color:
*Outer petal.*—Outside surface: Clove Pink, Plate 6, K–5. Inside surface: Red Cross, Plate 4, L–6.
*Inner petal.*—Outside surface: Garnet Red or Wild Strawberry, Plate 6, K–6. Inside surface: Flaming Maple, Plate 4, L–5.
General color effect:
*Newly opened flower:* Garnet Red, Wild Strawberry, Plate 6, K–6.
*Three days open:* Garnet Red, Plate 6, K–6 to Flaming Maple, Plate 4, L–5 toward center.
Behavior: Persist.
Flower longevity: cut roses grown in greenhouse kept at living room temperature 10 day in August.

*Reproductive organs*

Stamens: Many; arranged regularly, mixed with few petaloids.
Filaments: Many; with anthers; short.
*Color.*—Yellow-reddish.
Anthers: Open at various times; medium large.
*Color.*—Yellow-reddish.
*Seldom.*
Pollen: Abundant; orange yellow.
Pistils: Many; reddish style, yellow stigma.
Styles: Even; medium long, thin; bunched.
Stigma: Yellow.
Ovaries: Some protruding from receptacle.
Hips: Very short, with inconspicuous neck; smooth; no prickles; green.
Sepals: Permanent; long; spear shaped; phylid appendages.
Seeds: Medium number; medium size.

*Plant*

Foliage:
*Leaves.*—Compound of 3, 5, 7; normal; leathery, not glossy.

*Leaflets.*—Shape: ovoid, with apex obtuse; base round; margin simply serrate.

*Color.*—Mature—upper surface: dull green; under surface: grey green. Young—upper surface: reddish green; under surface: reddish green.

*Rachis (the supporting stem of the compound leaf).*—Light, weight. Upper side: few vestigials; prickly. Under side: smooth.

*Stipules.*—Vestigial; short length.

*Disease.*—Resistant to mildew.

Growth:

*Habit.*—Bushy; much branched.

*Growth.*—Vigorous.

*Canes.*—Medium heavy.

*Main stems.*—Dull. Color: green. Torns: up to ½ inch on base of shoots. Color: reddish green—turn brown. Hairs: none.

*Branches.*—Dull. Color: green. Thorns: few, up to ½ inch. Color: greenish yellow. Hairs: none.

*New Shoots.*—Dull. Color: reddish green. Thorns: few. Color: reddish. Hairs: none.

I claim:

1. A new and distinct variety of rose plant of the floribunda class substantially as herein shown and described, characterized particularly as to its hardy, tall growth for cut flowers, with the novelty of the blooms characterized by distinctive shades of red, which hold for a long time indoors, and have a slight spicy fragrance.

No references cited.

ROBERT E. BAGWILL, Primary Examiner